United States Patent [19]

Stevens et al.

[11] 4,290,775

[45] * Sep. 22, 1981

[54] ANALYTICAL METHOD FOR DETERMINING ACID/SALT AND BASE/SALT SPECIES CONCENTRATION IN SOLUTION

[75] Inventors: Timothy S. Stevens; Theodore E. Miller, Jr., both of Midland, Mich.

[73] Assignee: The Dow Chemical Co., Midland, Mich.

[*] Notice: The portion of the term of this patent subsequent to Apr. 22, 1997, has been disclaimed.

[21] Appl. No.: 115,837

[22] Filed: Jan. 28, 1980

[51] Int. Cl.³ ............... G01N 31/04; G01N 27/08
[52] U.S. Cl. ............................... 23/230 R; 210/662
[58] Field of Search ............... 23/230 R; 210/31 C, 210/656, 662

[56] References Cited

U.S. PATENT DOCUMENTS

| | | |
|---|---|---|
| 3,607,083 | 9/1971 | Chowdhry . |
| 3,897,213 | 7/1975 | Stevens . |
| 3,915,642 | 10/1975 | Small . |
| 3,918,906 | 11/1975 | Small . |
| 3,920,397 | 11/1975 | Small . |
| 3,950,137 | 4/1976 | Larson . |
| 4,165,219 | 8/1979 | Huber ........................... 23/230 R |
| 4,199,323 | 4/1980 | Miller ........................... 23/230 R |
| 4,242,097 | 12/1980 | Rich ........................... 210/656 X |

OTHER PUBLICATIONS

"Materials, Equipment & Systems for Chromatography Electrophoresis Immunochemistry and Membrane Filtration," Bio-Rad Lab, Price List C, pp. 6-15, Mar. 1977.

"Materials Equipment & Systems for Chromatography Eletrophoresis Immunochemistry and Membrane Filtration," Bio-Rad Lab, Price List E, pp. 1-26, Apr. 1979.

*Primary Examiner*—Sidney Marantz

[57] ABSTRACT

Analytical method based on converting an acid or base species to water or absorbing the acid species whereby the species of interest is no longer responsive to a detector. Interfering salt(s) is simultaneously converted to a detectable acid or hydroxide derivative(s) in whole or in part. The species of interest is determined indirectly by subtracting the response of the salt derivative (which is proportional to the original salt) from a pre-derivatization response which is proportional to the salt plus base or salt plus acid.

18 Claims, 5 Drawing Figures

ANALYTICAL METHOD FOR DETERMINING ACID/SALT AND BASE/SALT SPECIES CONCENTRATION IN SOLUTION

BACKGROUND OF THE INVENTION

The invention resides in an improved analytical method for determining hydrogen form acids and hydroxide form bases in the presence of salt interferences.

More specifically, the present invention resides in a flow injection method for determining acid or base species concentrations in the presence of salt, comprising the steps of injecting sample into an aqueous carrier, analyzing the sample in carrier solution and storing the resulting signal thereby generated, said signal being proportionate to the acid/salt or base/salt concentration of the sample, eluting the sample in carrier through an ion-exchanger effective to derivatize the acid or base species to water or absorb the acid species, and to derivatize the salt in whole or in part to a soluble hydroxide derivative or soluble hydrogen derivative, respectively, said elution step being carried out for acids in a basic ion-exchanger in the hydroxide ion form and/or free amine form and for bases in an acidic ion-exchanger in the hydrogen ion form, analyzing the effluent of the ion-exchanger to obtain a calibrated signal which is proportionate to the original salt concentration, and establishing the difference in signals to determine the acid or base species concentration in the original sample.

RELATED PRIOR ART

Differential conductivity methods for carrying out analytical determinations are known, as exemplified by U.S. Pat. Nos. 3,607,083 and 3,950,137. These methods depend on the addition of reagents to precipitate interfering ions and thus tend to be useful for only a relatively few ion species. Accumulation of the precipitate also produces instrument fouling problems which require periodic clean-ups and surveillance to maintain the instrument in working order.

Known ion-exchange chromatographic analytical techniques are relevant to the present invention since the chemical reactions performed may be similar to certain derivatization reactions practiced by this invention. The prior art is represented by the teachings of U.S. Pat. No. 3,920,397. Ion-exchange chromatographic techniques use an electrolyte carrier phase which is selected based on suitability to perform chromatographic separations. The present invention is not a chromatographic technique. In addition, the prior art technique is not suited for assaying acid or base samples directly, but is rather designed for detecting and quantitating chromatographically separated cation and anion species.

What may be referred to as total ionic content analyzers and single ion analyzers may also employ conductimetric detectors in combination with ion-exchangers. This prior art is taught in U.S. Pat. Nos. 3,897,213, 3,915,642 and 3,918,906 and is characterized generally by the conversion of a mixture of ionic species to a single, preselected species. The technique is used to maximize the accuracy of a conductimetric measurement. The present invention is distinguished over these different prior art methods which are not suitable for the quantitative analysis of acid or base species in acid/salt and base/salt sample matrices.

THE INVENTION

The present invention is based on flow injection of sample onto an ion-exchanger to convert acid or base species to water or absorb the acid species, whereby the species of interest is no longer responsive to a detector. In conjunction with this reaction, interfering salt(s) is simultaneously converted to a detectable acid or hydroxide derivative(s) in whole or in part. The species of interest is determined indirectly by subtracting the calibrated response of the salt derivative (which is proportional to the original salt) from a pre-derivatization signal which is proportional to the salt plus base or salt plus acid.

When a weak base ion-exchanger or exchange material in the free amine form is used for quantitating acid species, the acid of the sample is absorbed without the production of water and the salt of the sample may or may not be converted in whole to a hydroxide derivative depending on the characteristics of the weak base ion-exchanger used. Other forms of the invention are based on the production of water as the derivative of the species of interest rather than absorption phenomena.

Specifically, a strong base ion-exchanger removes the anions from the sample and returns to the sample an equal molar proportion of $OH^-$ ions, whereby the acid species of interest is derivatized to water, and the salt(s) to a detectable hydroxide(s). The mode for quantitating an aqueous base species relies on the inverse principle of eluting the sample through an acidic form ion-exchanger in the hydroxide ion form to strip the sample of essentially all cations, and return to the sample an equivalent proportion of hydrogen ions. Hence, the base is derivatized to water and is rendered indistinguishable from the water carrier phase and the salt(s) is derivatized to a detectable acid(s).

The use of ion-exchangers that contain a mixture of strong and weak base sites or strong and weak acid sites is also within the teaching of the present invention. Unless otherwise indicated, the terms "acid" and "base" whenever used herein denote sample species with a $pK_a$ and $pK_b$ of less than about 5. Preferred applications are taught with respect to acids and bases of a $pK_a$ and $pK_b$ of less than about 2.

A pair of conductivity cells of the flow-through design are preferably used to determine the conductimetric response of the sample and ion-exchange effluent, i.e., salt derivative, respectively. With double pass-through techniques, a single cell can be suitably employed in an equivalent mode. A diffuser column or static mixer is preferably employed upstream of a first of said detectors to produce a repeatably diluted distribution of the sample in the carrier. Employment of the diffuser column is desirable since response linearity is improved at the resulting lower sample ion concentrations. Peak picker electronics are preferably utilized to store and compare the calibrated responses of the conductivity cells, using the criteria of the differential in peak height, to estimate base or acid concentration. Alternatively, the peaks may be integrated and the difference in the calibrated peak area (as opposed to peak height) used to quantitate the acid or base species concentration. The salt concentration may be simultaneously determined since it is proportional to the effluent peak (provided the salt mixture remains known and thus calibratable).

Alternate detector forms which may be set up to operate using the differential response principle described in detail above, would desirably include, by way of example, flow-through polarographic cells, differential refractometers, ion specific electrodes, spectrophotometers, and such other detectors as are capable of suitably quantifying the salt derivative involved, and acid/salt or base/salt involved. The preferred differential conductimetric detection mode is ideally suited for use in applications generally described by the condition wherein the acid and salt or base and salt mixture is more than 50% dissociated ionically in the diluted sample/eluent stream at the critical point of the first detection step (referring specifically to the ionic dissociation in the area of maximum sample concentration).

The preferred apparatus for practicing the invention is shown in the following drawings wherein.

Figure 1:
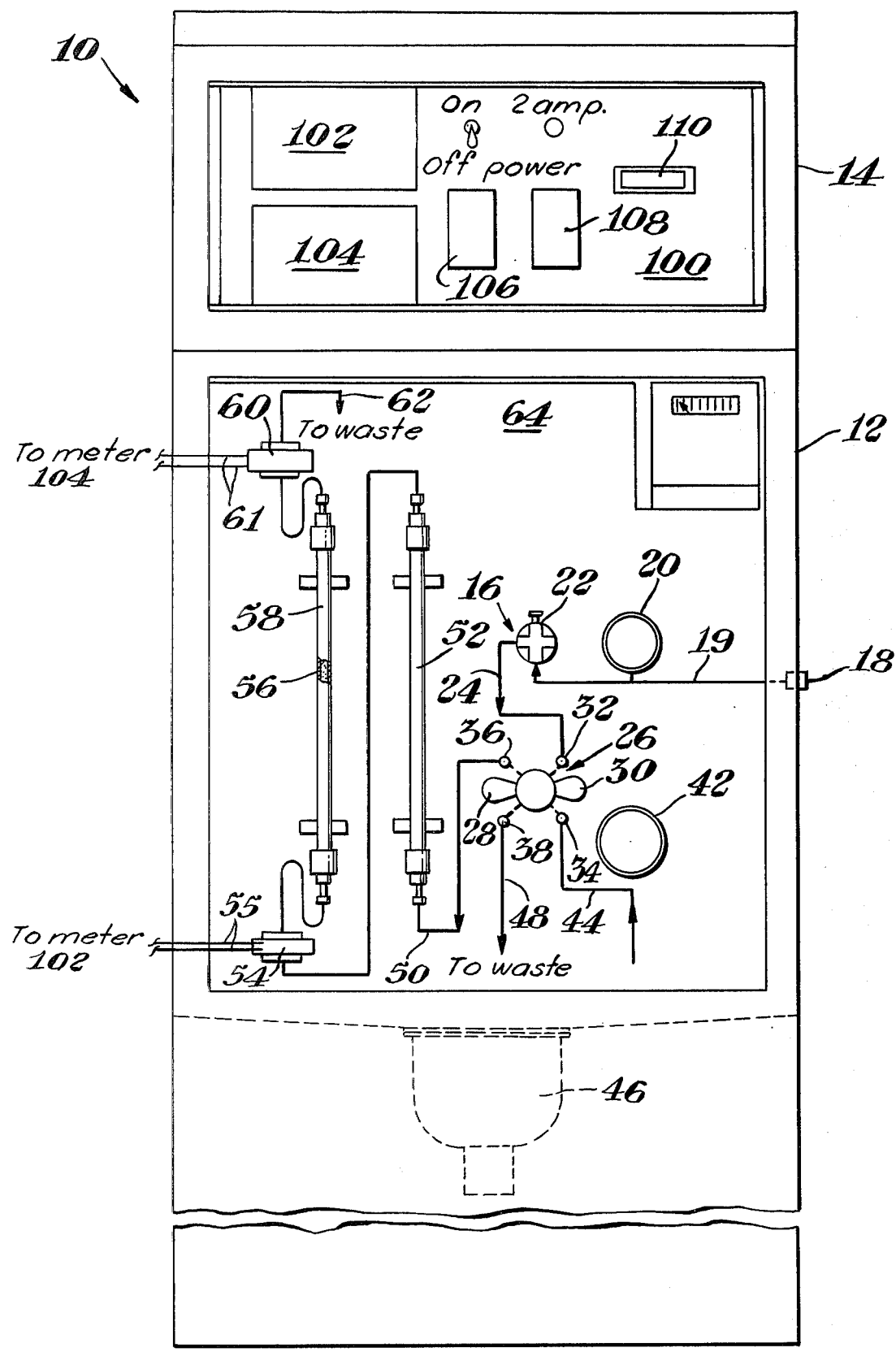
FIG. 1 is an elevation view of an analytical instrument constructed according to the principles of the invention.

The instrument 10, shown in FIG. 1, comprises a lower cabinet 12 containing a 3-way manual selector valve 16 (preferably a product code No. 201-54 slider valve from Altex Corp.). A sample entry fitting 18 is connected to conduit 19 for admitting a sample stream to the valve 16. A pressure gauge 20 is provided in conduit 19 to give a continuous reading of the sample pressure.

The selector valve 16 includes an auxiliary port 22 for manually admitting standards by the syringe loading technique. The valve selectively routes the sample stream or the standard through an outlet line 24 to a pneumatically operated double acting sample injection valve 26 defining a carrier loop 28 and a sampling loop 30. Injection valve 26 (preferably an Altex Code No. 201-56 valve with Altex Code No. 201-12 pneumatic actuators) is equipped with a sample inlet 32, a carrier inlet 34, a sample/carrier outlet 36, and a sample purge outlet 38. An eluent or carrier stream is admitted continuously to carrier inlet 34 via a metering pump 40 (preferably a Milton Roy Simplex Mini-pump, Model No. 396-31), and a carrier inlet line 44 (see also FIG. 2). A pressure gauge 42 is provided in line 44 for giving a continuous pressure readout. The eluent from inlet 34 is routed through carrier loop 28 to the sample/carrier outlet 36. The sample from sample inlet 32 is routed either through sampling loop 30 to sample purge outlet 38 or a loop-captured sample aliquot is flushed from the sample/carrier outlet 36, depending on the valving position. The purge outlet 38 communicates through an outlet line 48 with a waste sump 46. The sample/carrier outlet 36 communicates through a second outlet line 50 with a resin packed diffuser column or static mixer 52. The diffuser column is serially connected with a flow-through conductivity cell 54, a derivatization column 58 packed with ion-exchange beads 56, and a second flow-through conductivity cell 60. Ultimately, the spent sample is disposed of to waste sump 46 through an outlet line 62.

Strong acid form ion-exchange resins in the hydrogen ion form and useful in the apparatus of the present invention for analyzing base species are, for example, the commercially trade-designated AG50WX16 resin, from Bio-Rad Lab., Richmond, Calif., the Amberlite ® IR-120 resin from Rohm & Haas, and the Dowex ® type 50WX16 resin from The Dow Chemical Company (all resins are preferably of 200 to 400 standard U.S. mesh size, sulfonated, cross-linked, divinyl benzene, strongly acidic cation exchange resins). Strong base form ion-exchange resins in the hydroxide ion form for quantitating aqueous acid species and useful in the apparatus of the present invention are the trade-designated AG1X10 resin from Bio-Rad, the Amberlite ® IRA-400 resin and the Dowex ® 1-X10 resin, (all resins are preferably of 200 to 400 standard U.S. mesh size and animated, cross-linked, divinyl benzene, strongly basic anion exchange resins, requiring conversion to the hydroxide form by washing with sodium hydroxide solution according to known technique). The commercially available ion-exchange resins, supra, are described and characterized in further detail in the publication "Materials, Equipment and Systems for Chromatography Electrophoresis Immunochemistry and Membrane Filtration", Bio-Rad Lab., Price List C, (March 1977), pp. 6–15.

Weak acid form ion-exchange resins in the hydrogen ion form and useful in the apparatus of the present invention for analyzing base species are, for example, the commercially trade-designated Bio-Rex 70 resin, from Bio-Rad Lab., Richmond, Calif., and the Amberlite ® IRC-50 resin from Rohm & Haas (all resins are preferably of 200 to 400 standard U.S. mesh size). Weak base ion-exchange resins in the free amine ion form for quantitating aqueous acid species and useful in the apparatus of the present invention are the trade-designated AG3-X4A resin from Bio-Rad, and Amberlite ® IR-45 resin (all resins are preferably of 200 to 400 standard U.S. mesh size requiring conversion to the free amine form by washing in sodium hydroxide solution according to known technique). The commercially available ion-exchange resins, supra, are described and characterized in further detail in the publication "Materials, Equipment and Systems for Chromatography Electrophoresis Immunochemistry and Membrane Filtration," Bio-Rad Lab., Price List E, (April 1979), pp. 1–26.

Figure 2:
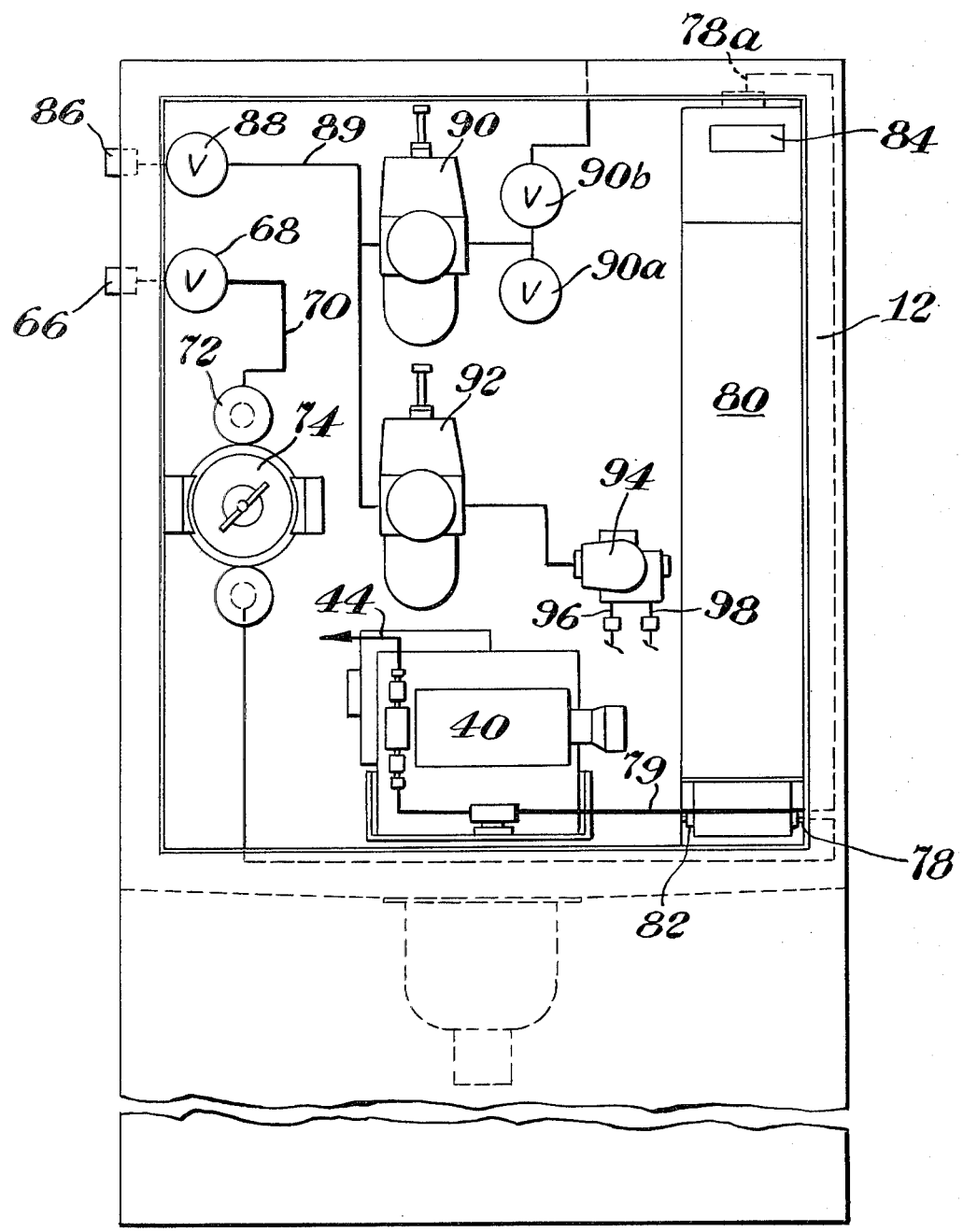
FIG. 2 shows hidden detail of the instrument of FIG. 1 and is also an elevation view.

In respect now to the further components of instrument 10 shown in FIG. 2, the concealed portion of the lower cabinet 12 includes an inlet fitting 66 for admitting tap water through a shut-off valve 68 connected by an inlet line 70 to a line pressure gauge 72, a diaphragm type pressure regulator 74, and a second line pressure gauge 76. The tap water is supplied to the inlet 78 of a water purifying column assembly 80, equipped with a bottom drain 82 and a conductivity meter 84 (the column assembly 80 is commercially available under the code designation DO800B and includes a Code No. DO803 cartridge, from Barnstead Co., Boston, MA). A column assembly outlet 78($a$) is connected by conduit 79 to injection valve 26 through metering pump 40, as described.

An air inlet fitting 86 communicates through a pneumatic shut-off valve 88 and conduit 89 with a pair of air pressure regulators 90 and 92 of conventional design and connected in parallel. Regulator 90 is connected to needle valves 90($a$) and 90($b$) which, in the open position, purge both the lower and upper cabinet spaces, respectively, with a corrosion inhibiting clean air stream. Regulator 92 supplies air to a 4-way solenoid valve 94 which is connected, by means of connectors 96 and 98, to pneumatic actuators of the sample injection valve 26.

Referring to FIG. 1, the upper cabinet 14 houses a panel 100. Conductivity meters 102 and 104 are mounted on panel 100 and monitor the response of conductivity cells 54 and 60, respectively, by converting the conductimetric response of the cells to an analog D.C. voltage output signal. A pair of solid state time delay relays 106 and 108 (which preferably are of the Type 328 A 200 Q10XX relays commercially available from Newark Electronics, Detroit, MI), provide a variable injection cycle to actuate the injection of a sample and to reset the peak picker circuits, as will be described hereinafter. A readout analog voltage meter 110 displays the differential output signal of the dual peak picker circuits of the circuitry described below.

Figure 3:
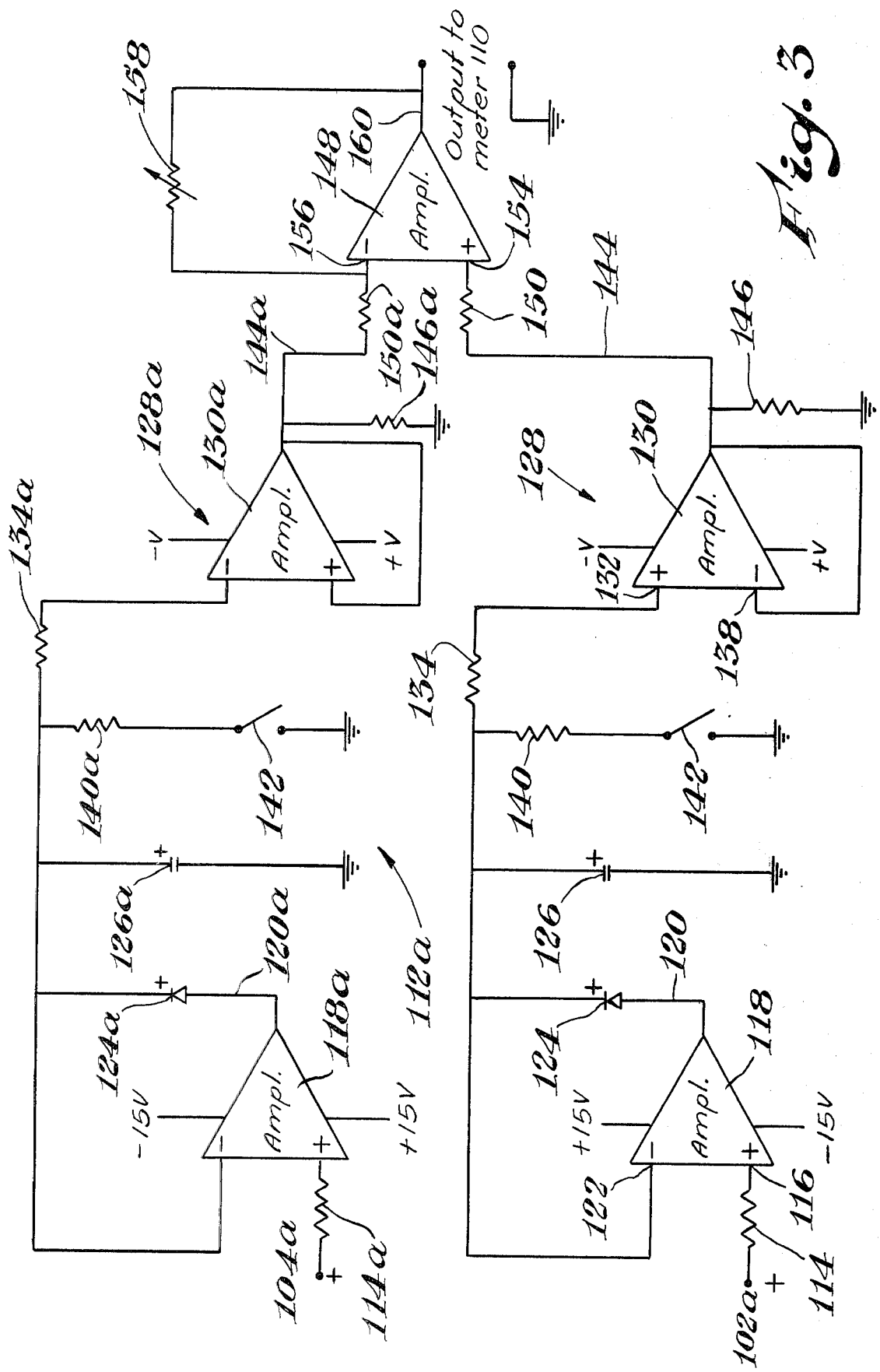
FIG. 3 is a circuit diagram of the apparatus.

The electronic control circuit comprises dual peak picker circuits 112 and 112(a), shown in FIG. 3, which receive the analog D.C. output signals from meters 102 and 104 at terminals 102a and 104a, respectively. The circuits 112 and 112(a) are identical so that the components of circuits 112(a) are identified by like reference numerals as the components of circuit 112, but with the suffix "a" added after each reference number.

Circuit 112 comprises a resistor 114 which is connected to a FET input operational amplifier 118 having a noninverting input terminal 116 and an inverting terminal 122 (commercially available under product Code No. BB 3308 from the Burr-Brown Research Corp., Tucson, AZ), with a ±15 D.C. volt power supply (not shown) and preferably an Acopian Model D-15-15A. The output lead 120 of amplifier 118 is connected to its inverting input terminal 122 through a diode 124. The capacitor 126 maintains a voltage value equal to the most positive value attained on the noninverting input terminal 116. The information on the capacitor distinguishes the peak voltage of the output signal from conductivity meter 102 for each sample reading. This information is processed and detected by a unity gain buffer amplifier circuit 128 which comprises a second FET operational amplifier 130 (preferably also of the type BB 3308). Capacitor 126 is connected to a noninverting input terminal 132 of amplifier 130, through a resistor 134, and the output of amplifier 130 is directly connected to an inverting input terminal 138. The capacitor 126 is reset by a shunted resistor 140 which is connected in series with a switch 142.

Output lines 144 and 144(a) of each peak picker circuit 112 and 112(a) are connected to ground through a load resistor 146 and 146(a), respectively, to stabilize the output from drift. The output lines 144 and 144(a) are connected to an operational amplifier 148 (preferably a type 741), through resistors 150 and 150(a), respectively. Thus, circuit 112 is connected to a noninverting input 154 of amplifier 148, and circuit 112(a) is connected to an inverting input 156 of amplifier 148. A variable resistor 158 is connected between output line 160 and inverting terminal 156 of amplifier 148 to produce a differential amplifier that amplifies the differential voltage between output lines 144 and 144(a). The differential output signal is displayed on readout panel meter 110.

As a part of the instrument calibration for samples of totally unknown composition, a standard is prepared of the salt constituent, omitting the base or acid of interest. The calibration standard is injected manually via a syringe into auxiliary port 22 of selector valve 16. Conductivity meter 104 is adjusted so that the final readout on voltage meter 110 is zero, after complete sample analysis. Since the derivative acid or base of the salt constituent is usually more responsive, the step will normally require a reduction of sensitivity of the second conductivity meter 104 relative to meter 102. A calibration curve is also prepared by means of injecting a series of acid/salt or base/salt standards of varying concentrations over the range of interest. When the sample is composed of essentially constant total ionic content but varying levels of salt and base or acid such as in chlor-alkali cell effluents or acid or caustic scrubbers, then calibration with standards containing a mixture of salt and acid or base of total ionic content similar to the sample results in more accurate calibration of the instrument, insuring errors of less than 2% relative. The calibrated instrument is then prepared for use in the mode described below.

A sample stream is continuously admitted through conduit 19. The sample stream is passed through injection valve 26 to waste sump 46. Simultaneously, tap water is continuously admitted through inlet 78 and purifying column 80 and monitored for ionic purity by conductivity meter 84. The resulting purified eluent stream is conveyed from the column outlet 78(a) of the water purifying assembly 80 by pump 40 through conduit 79 to the injection valve 26 and hence through carrier loop 28, carrier/sample outlet 36 and line 50 through columns 52 and 58 and conductivity cells 54 and 60 to the waste sump 46. Timer 108 establishes the overall cycle time, and can be set to repeat the cycle at predetermined intervals. Timer 106 can also be set to determine the duration of injection and to reset the peak picker circuits through switches 142 and 142(a). Following this pattern, timer 106 signals injection valve 26 to inject a sample aliquot into the carrier or eluent stream entering inlet 34. At the same moment, timer 106 activates conventional relays (not shown) to close switches 142 and 142(a), thereby resetting circuits 112 and 112(a) for the analysis of the current sample.

The injected sample first passes through the diffuser column 52 typically diluting the samples concentration (in an approximate Gaussian distribution) approximately 80 times at the peak maxima. The sample then passes to the first conductivity cell 54. The reading from the cell 54, (a non-displayed signal indicative of total ionic content) is conducted to circuit 112, through conductivity meter 102. The voltage signal from the meter 102 is held at a maximum positive value by the capacitor 126 of peak picker circuit 112. Thus, this information is stored (memorized by the peak picker circuit), and conducted to line 144.

The sample is then passed to the derivatizing column 58. Assuming that the sample contains base, the cations are exchanged at the active exchange sites of the exchange resin for hydrogen (hydronium) ions, thus being captured and removed from the effluent of the derivatizing column, and the hydroxide ions are converted to $H_2O$ thus blending into the deionized eluent stream. The salt is correspondingly converted to its acid derivative and the salt cations are captured at the column's active ion-exchange sites.

The ion-exchange effluent is passed directly to the second conductivity cell 60, and the information is conducted through meter 104 to terminal 104(a) of peak picker circuit 112(a). Capacitor 126(a) stores the maximum positive voltage input value which is also applied to line 144(a) through amplifier 130(a). The differential amplifier circuit, through voltage meter 110, displays the differential value of the peak picker circuit outputs from which value the species concentration may thus be predicted. Timer 108, after a predetermined period of time, discontinues its timing function and resets timer 106. Timer 106 activates valve 16 to admit the next sample into the eluent stream for automatic analysis of the succeeding sample.

Figure 4:
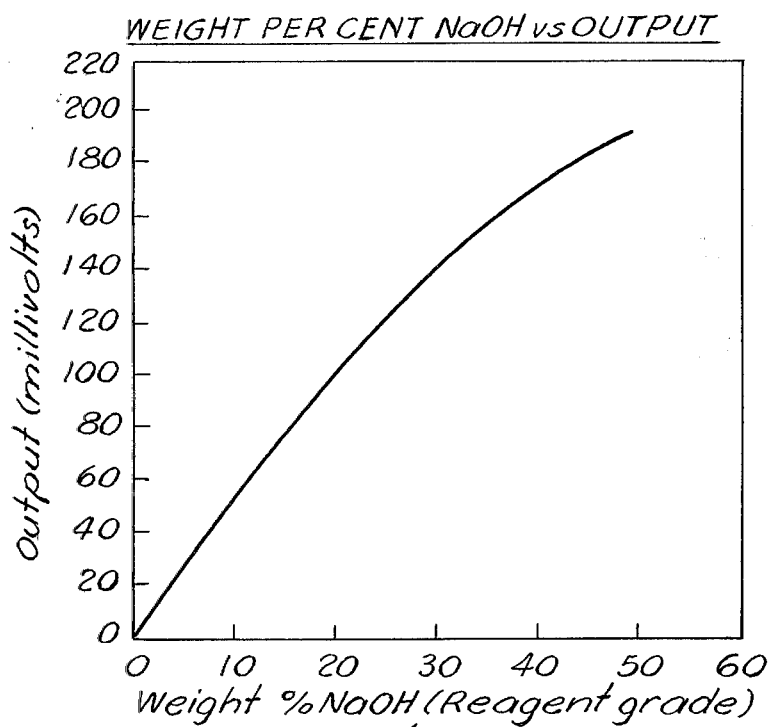
FIGS. 4 and 5 are reproductions of a typical calibration curve and a strip chart of instrument output.

FIG. 4 is a plot of a typical calibration curve developed by using a series of NaOH standards. Injected standards range up to the 50 percent concentration level. The described analytical technique is considered useful, however, up to the solubility limits of the acid or base sample constituents. Linearity, while not absolute, hence does not show loss of sensitivity (i.e., excessive curve flattening). It may also be observed that for a typical process application wherein the concentration ranges from 0 to 20 percent, errors as might be introduced in assuming linearity would not be great. Thus, it is apparent that applications exist where the concentration may be directly reported by the instrument by calibrating at a single point only. Thus, response curve linearization electronic circuits or their equivalent are not necessarily required in the practice of the invention.

Figure 5:
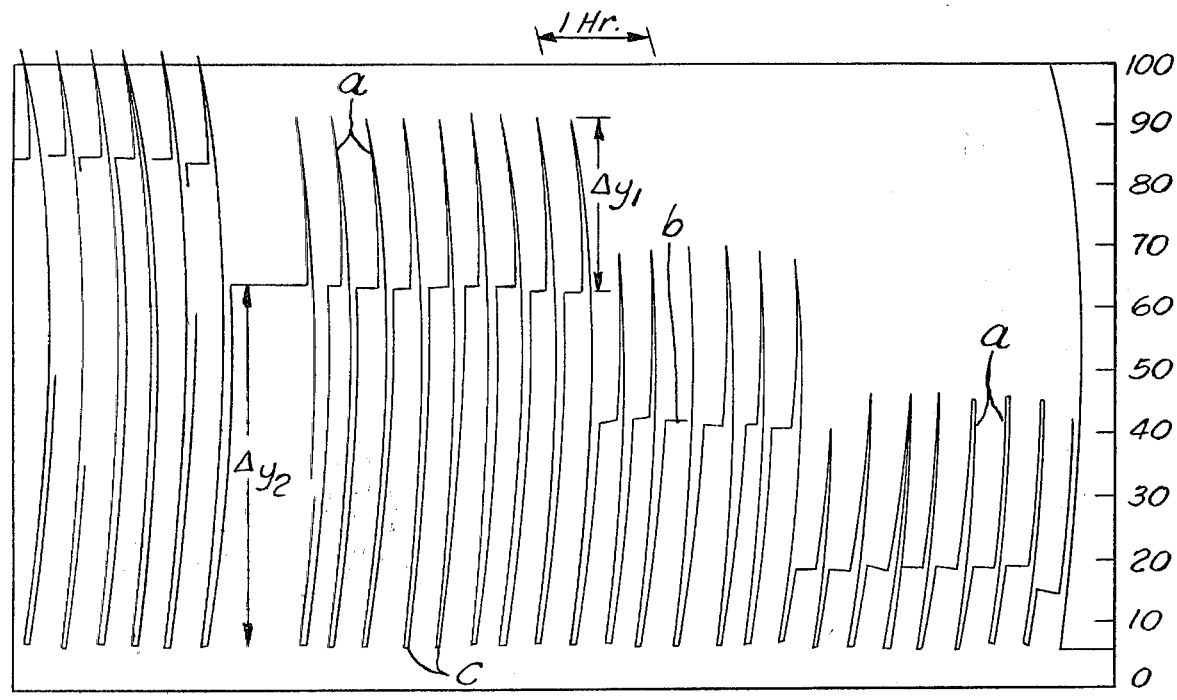

Also, in the usual mode, the instrument may be monitored by suitable hard copy chart recorders to produce strip chart output data forms as generally illustrated by FIG. 5. By way of example, the following experiment was conducted.

EXPERIMENT I

Eluent: Deionized water
Flow Rate: 84 ml/hour
Injector Volume: 3.8 μl
Injection Frequency: 18 min.
Diffuser Column: 9×250 mm glass column packed with Rohm & Haas XAD-2 resin packing, 80 to 120 mesh
Ion-Exchange Column: 9×250 mm glass column packed with Bio-Rad 50WX16 resin packing, 200 to 400 mesh in the hydrogen ion form
Detectors: Model BM-2 conductivity meters from Modern Metalcraft, Midland, Mich. with 2 μl Wescan Model No. 219-200 flow-through conductivity cells The data of FIG. 5 is generated using the denoted caustic-salt standard solutions (reagent grade) admitted by injection of a sample with a syringe which explains the cause of the slight discrepancy indicated by the first peak at the right side of the chart (caused by insufficient initial flushing of the loop). The base line (c) indicates the differential output resulting from the peak picker reset at the injection time zero. The salt spike or (a) represents the maximum conductivity value reported during sample elution through cell 54, and hence represents combined salt and base response. The reduction to plateau (b) is the consequence of the salt derivative peak elution through cell 60, and hence the value $\Delta Y_2$ (i.e., total ionic less the salt derivative response) may be used to estimate the base concentration. By the same token, the value $\Delta Y_1$ is proportionately related to the salt concentration, and thus predicative thereof. Similarly, in the case of a mixture of bases and salts or acids and salts, the technique described would, by the same procedure and data, predict total acid or total base (and total salt) concentration.

EXPERIMENT II

The experiment of FIG. 5 is repeated using a series of reagent grade NaOH reagent standard solutions in concentrations which increase in increments of 0.5 N NaOH from 0.5 N to 2.0 N, omitting the salt constituent. Similar results are observed except without a detectable salt spike (a) in the strip chart output. The absence of an apparent salt spike thus confirms that essentially no detectable caustic derivative, or caustic, or column residue interferences elute from the ion-exchange means. Hence, essentially the total caustic content of the sample is successfully derivatized to water using the recommended ion-exchange resin, supra.

EXPERIMENT III

The experiment of FIG. 5 is repeated except that the weak acid resin Bio-Rex 70 is substituted for Bio-Rad 50WX16, with essentially similar results.

EXPERIMENT IV

Analysis of reagent grade HCl samples (not containing any salt constituent) under exactly the same conditions as the FIG. 5 experiment, supra, demonstrates that no detectable unreacted acid elution is obtained using an AG1X10 ion-exchange resin of 200 to 400 U.S. standard mesh size converted to the OH⁻ form by washing with sodium hydroxide solution. This experiment thus demonstrates excellent suitability of purpose of this ion-exchange resin for acid analysis. Some unreacted acid passing through the ion-exchange resin is detected under exactly the same operating conditions except that an AG1X8 resin of 20 to 50 U.S. standard mesh size is used. Both resins are commercially available. The results with the AG1X8 resin are attributed principally to improper mesh size and, therefore, use of the preferred AG1X10 resin, 200 to 400 mesh size, for acid/salt analysis is recommended.

EXPERIMENT V

The experiment of FIG. 5 is repeated except that the weak base resin Bio-Rad AG-3X4A is substituted for Bio-Rad AG1X10 with essentially similar results.

What is claimed is:

1. A flow injection method for determining acid or base species concentration in the presence of salt, comprising the steps of injecting sample into an aqueous carrier, analyzing the sample in carrier and storing the resulting signal thereby generated, said signal being proportionate to the acid/salt or base/salt concentration of the sample, eluting the sample in carrier through an ion-exchanger effective to derivatize the acid or base species to water or absorb the acid species, and to derivatize the salt in whole or in part to a soluble hydroxide derivative or soluble hydrogen derivative, respectively, said elution step being carried out for acids in a basic ion-exchanger in the hydroxide ion form and/or free amine form and for bases in an acidic ion-exchanger in the hydrogen ion form, analyzing the effluent of the ion-exchanger to obtain a calibrated signal which is proportionate to the original salt concentration, and establishing the difference in signals to determine the acid or base species concentration in the original sample.

2. The method of claim 1 wherein said injection and elution step employ as the carrier deionized water.

3. The method of claim 1 wherein said signals are obtained in response to electrolytic conductivity of the sample solution.

4. The method of claim 1 wherein the acid/salt or base/salt is characterized by an ionic dissociation of greater than 50% in the carrier eluent at the location of the first conductimetric determination, said 50% ionic dissociation referring to the area of maximum concentration of the sample solution in the carrier eluent.

5. The method of claim 4 wherein said sample is injected into a flowing carrier stream, and including the step prior to said first conductimetric analysis step, of diffusing the sample solution to produce a diluted distribution of the sample solution within the surrounding carrier eluent.

6. The method of claim 1 wherein the acid or base species is characterized by a $pK_a$ of less than about 2.

7. The method of claim 1 analyzing for acid species and wherein said derivatization step is carried out in a basic ion-exchange material in the free amine form.

8. The method of claim 7 wherein said injection and elution step employ as the carrier deionized water.

9. The method of claim 7 wherein said signals are obtained in response to electrolytic conductivity of the sample solution.

10. The method of claim 7 wherein the acid/salt or base/salt is characterized by an ionic dissociation of greater than 50% in the carrier eluent at the location of the first conductimetric determination, said 50% ionic dissociation referring to the area of maximum concentration of the sample solution in the carrier eluent.

11. The method of claim 10 wherein said sample is injected into a flowing carrier stream, and including the step prior to said first conductimetric analysis step, of diffusing the sample solution to produce a diluted distribution of the sample solution within the surrounding carrier eluent.

12. The method of claim 7 wherein the acid or base species is characterized by a $pK_a$ of less than about 2.

13. The method of claim 1 analyzing for base species wherein said derivatization step is carried out in a weak acid ion-exchange material in the hydrogen ion form.

14. The method of claim 13 wherein said injection and elution step employ as the carrier deionized water.

15. The method of claim 13 wherein said signals are obtained in response to electrolytic conductivity of the sample solution.

16. The method of claim 13 wherein the acid/salt or base/salt is characterized by an ionic dissociation of greater than 50% in the carrier eluent at the location of the first conductimetric determination, said 50% ionic dissociation referring to the area of maximum concentration of the sample solution in the carrier eluent.

17. The method of claim 16 wherein said sample is injected into a flowing carrier stream, and including the step prior to said first conductimetric analysis step, of diffusing the sample solution to produce a diluted distribution of the sample solution within the surrounding carrier eluent.

18. The method of claim 13 wherein the acid or base species is characterized by a $pK_a$ of less than about 2.

* * * * *